United States Patent [19]
Yazaki et al.

[11] Patent Number: 5,750,825
[45] Date of Patent: May 12, 1998

[54] MOUSE WITH DEFECTIVE ENDOTHELINE-1 GENE FUNCTION

[75] Inventors: Yoshio Yazaki; Hiroki Kurihara; Yukiko Kurihara, all of Tokyo; Hiroshi Suzuki, Shizuoka; Tatsuhiko Kodama, Tokyo, all of Japan

[73] Assignee: Chugai Seiyaku Kabushiki Kaisha, Tokyo, Japan

[21] Appl. No.: 325,181

[22] PCT Filed: Oct. 21, 1993

[86] PCT No.: PCT/JP93/01522

§ 371 Date: Apr. 24, 1995

§ 102(e) Date: Apr. 24, 1995

[87] PCT Pub. No.: WO94/09621

PCT Pub. Date: May 11, 1994

[30] Foreign Application Priority Data

Oct. 23, 1992 [JP] Japan ..................... 4-286131

[51] Int. Cl.⁶ .................... C12N 5/00; C12N 15/00; C12N 15/09
[52] U.S. Cl. ............ 800/2; 800/DIG. 1; 800/DIG. 2; 800/DIG. 3; 435/172.3; 435/325; 435/320.1; 935/53; 935/70
[58] Field of Search .................... 800/2, DIG. 1, 800/DIG. 2, DIG. 3; 435/172.3, 320.1; 935/53, 70

[56] References Cited

U.S. PATENT DOCUMENTS 5,416,260  5/1995  Koller et al. ..................... 800/2

FOREIGN PATENT DOCUMENTS 1-233297  9/1989  Japan.
3-201990  9/1991  Japan.

OTHER PUBLICATIONS

Bradley et al., BioTechnology 10:534–539 (1992).
Yanagisawa et al., Nature 332: 411–415 (1988).
Blaine et al., "Clinical and Therapeutic Implications of New Peptides in Hypertension", Current Opinion in Cardiology, vol. 6, No. 5, (1991), pp. 686–692.

*Primary Examiner*—Jasemine C. Chambers
*Assistant Examiner*—Jill D. Schmuck
*Attorney, Agent, or Firm*—Foley & Lardner

[57] ABSTRACT

There is provided a mouse lacking the function of the endotheline-1 gene by insertion of another gene into the endotheline-1 gene.

The mouse is useful for elucidation of the pathological physiology and causes of and development of therapies for cardiovascular diseases such as hypertension, arteriosclerosis and ischemic heart disease.

5 Claims, 1 Drawing Sheet

MOUSE WITH DEFECTIVE ENDOTHELINE-1 GENE FUNCTION

This application is a 371 of International Application Serial No. PCT/JP93/01522 filed on Oct. 21, 1993 which claims priority to the Japanese Application Serial No. 4-286131 filed on Oct. 23, 1992.

TECHNICAL FIELD

The present invention relates to a heretofore undocumented novel animal strain and to a method for producing it.

The animal of the present invention is a mouse for experimentation and research, a portion of whose endotheline-1 structural gene has a mutation. The peptide synthesis therefrom is suppressed as a result. This characteristic renders it extremely useful as an experimental animal for research toward elucidation of the pathological physiology and causes of and development of therapies for cardiovascular diseases such as hypertension, arteriosclerosis and ischemic heart disease.

BACKGROUND ART

A number of cardiovascular-active substances are receiving attention for their role in the pathological physiology of cardiovascular diseases such as hypertension, arteriosclerosis and ischemic heart disease. One of these, endotheline, is a 21-amino acid vasoconstrictor peptide isolated and purified from cardiovascular endothelial cells, and its nature was elucidated in 1988 (Yanagisawa, M., Kurihara, H., Kimura, S. et al. Nature 332:411, 1988).

The histological distribution of endotheline is so wide as to include the heart, kidney, adrenal, lungs, brain, etc. Its activity sites are also as varied as its histological distribution, including smooth muscle, vascular endothelium, cardiac muscle, the kidney, adrenal, central nervous system, etc. Attempts to delineate the physiological function of endotheline have been made by way of pharmacological tests, biochemical analyses and clinical research, but as yet the nature thereof has not been ascertained. Furthermore, there has not been available a mouse with defective endotheline gene function which is necessary for elucidation of the physiological function thereof.

In light of these circumstances, the present inventors have prepared a mouse lacking the gene for a cardiovascular-active substance and analyzed the resulting changes in physiological function including hemodynamics, thus allowing direct understanding of the physiological role of the cardiovascular-active substance while also providing an animal model with a well-defined genetic background for research toward the pathological elucidation of and methods of therapy for cardiovascular diseases.

DISCLOSURE OF THE INVENTION

Consequently, the present invention provides a mouse which has been genetically engineered to artificially lack the endotheline-1 gene (ET-1 gene) function.

DETAILED DESCRIPTION OF THE INVENTION

In order to obtain a mouse artificially lacking the endotheline-1 gene function, there was employed a method by which the endotheline-1 gene was cloned, inactivated in vitro by some method and then returned to the mouse. The cloning of the endotheline-1 gene may be carried out by, for example, extracting genomic DNA from mouse liver, preparing a DNA library in the conventional manner, and then screening DNA, for example, cDNA (See Yanagisawa, M., Kurihara, H., Kimura, S. et al. Nature 332:411, 1988) coding for endotheline-1 which has already been cloned therefrom.

Figure 1:
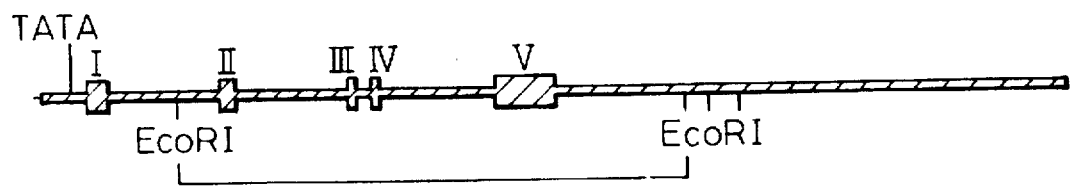
FIG. 1 shows the structure of the mouse genomic ET-1 gene fragment. The Roman numerals I to V in FIG. 1 indicate exon Nos. 1 to 5.

As shown in FIG. 1, the gene for the endotheline-1 precursor contains the 5 exons I to V, and endotheline-1 itself is encoded by exon No. 2. The function of the endotheline-1 gene may be rendered defective either by deleting one of the portions of the gene coding for the endotheline-1 precursor (hereunder referred to simply as "endotheline-1 gene") or by inserting another gene at one of the sites; however, it is preferable to insert another gene which also functions as a genetic marker for detection of the defective endotheline-1 gene, and such genes which may be used include a neomycin-resistance gene (selected by G418 resistance), a thymidine kinase gene (selected by ganciclovir resistance), a diphtheria toxin A fragment gene, and combinations of these. The insertion site is not particularly limited. The insertion of these genes may be accomplished in vitro by a commonly used DNA recombination technique.

Next, DNA for the homologous recombination obtained in this manner is introduced into mouse embryonic stem cells (ES cells), and homologous recombination is performed with the endotheline-1 gene in the ES cells. The insertion of DNA for the homologous recombination may be carried out by, for example, conventional electroporation. In this homologous recombination, recombination occurs between the DNA of the endotheline-1 genes in the ES cells and the corresponding region of DNA for the homologous recombination, and the marker gene inserted into the homologous recombination DNA is in turn inserted into the genomic endotheline-1 genes of the ES cells. As a result, ES cells come to lack the endotheline-1 gene, while acquiring the marker gene. ES cells lacking the endotheline-1 gene may then be obtained on the basis of the marker gene.

Next, ES cells are injected into a mouse blastocyst which is then transplanted into the uterine horn of a pseudopregnant mouse to obtain offspring. The chimeric mouse obtained in this manner is in turn crossed with a mouse of an appropriate strain to obtain offspring. If the germ cells of the chimeric mouse derive from the homologous recombinant (with the destroyed ET-1 gene) then a mouse with the destroyed ET-1 gene has been obtained.

A simplified explanation of each of the steps of the above-mentioned method will be given and followed by an explanation of the specific procedures.

1) Preparation of a mouse endotheline-1 (ET-1) gene DNA construct for homologous recombination A partial sequence of mouse ET-1 cDNA was hybridized as a probe to a genomic library prepared by partial digestion of genomic DNA extracted from mouse liver using a restriction endonuclease, and a positive clone was obtained. This was introduced into a vector, after which digestion was performed with a restriction endonuclease and genomic DNA with a total length of 7.5 kb containing exon No. 2 through exon No. 5 was subcloned.

Next, a neomycin-resistance gene and a thymidine kinase gene were inserted, in order to destroy the structure of the ET-1 gene and for positive/negative selection according to the method reported by Mansour et al. (Mansour, S. L., Thomas, K. R. & Capacchi, M. R., Nature 336:348–352, 1988).

2) ET-1 gene deletion in ES cells by homologous recombination

The construct DNA for homologous recombination was suspended in an electroporation buffer containing mouse embryonic stem cell (ES cell) strain A3-1 (Azuma & Toyoda, Jpn. J. Anim. Reprod. 37, 37–43, 1991), for introduction of the gene. Selection culture was then performed using G418 and ganciclovir. Identification of the homologous recombinants of the G418- and ganciclovir-resistant colonies was effected by PCR and Southern blotting.

3) Preparation of chimeric mouse with endotheline gene-deficient ES cells a) Karyotype analysis of endotheline gene-deficient ES cells and assay of differentiation potency in a suspension culture The endotheline gene-deficient ES cell strain confirmed to be a homologous recombinant was used to prepare a chromosome sample, and the proportion of cells with 2n=40 chromosomes, the normal mouse karyotype, was calculated. Also, endotheline gene-deficient ES cell strain was observed for embryoid body formation potency.

b) Injection of endotheline gene-deficient ES cells into blastocysts

ES cells confirmed to be normal by karyotype analysis and assay of differentiation potency were injected into C57BL/6J mouse blastocysts which were then transferred into the uterine horn of pseudopregnant mice to obtain offspring.

4) Assay of germline transmission of homologous recombinant in chimeric mice

The chimeric mice obtained by embryo transfer were crossed with 129/J or ICR mice and it was determined whether endotheline gene-deficient ES cell-derived offspring were obtained. If the germ cells of the chimeric mice are derived from the homologous recombinant, then the coat color of the delivered offspring is albino, while if they are derived from the blastocyst of C57BL/6J mice, they are the agouti. Also, blood was taken after weaning and the DNA thereof was extracted, and then PCR was performed by the method described above to confirm deletion of the endotheline gene.

SPECIFIC PROCEDURES (1) Preparation of a mouse endotheline-1 (ET-1) gene DNA construct for homologous recombination A partial sequence of mouse ET-1 cDNA was hybridized as a probe to the genomic library EMBL (provided by Prof. Kiyoshi Miyakawa of Tokyo Univ., 3rd Dept. of Internal Medicine) prepared by partial digestion of genomic DNA extracted from BALB/c mouse liver using restriction endonuclease Sau3AI, and after screening 1,000,000 colonies, one positive clone was obtained. This was inserted into λ-E10, and then digestion was performed with restriction endonuclease EcoRI and genomic DNA with a total length of 7.5 kb containing exon No. 2 through exon No. 5 was subcloned (pE10-29) (FIG. 1).

Figure 2:
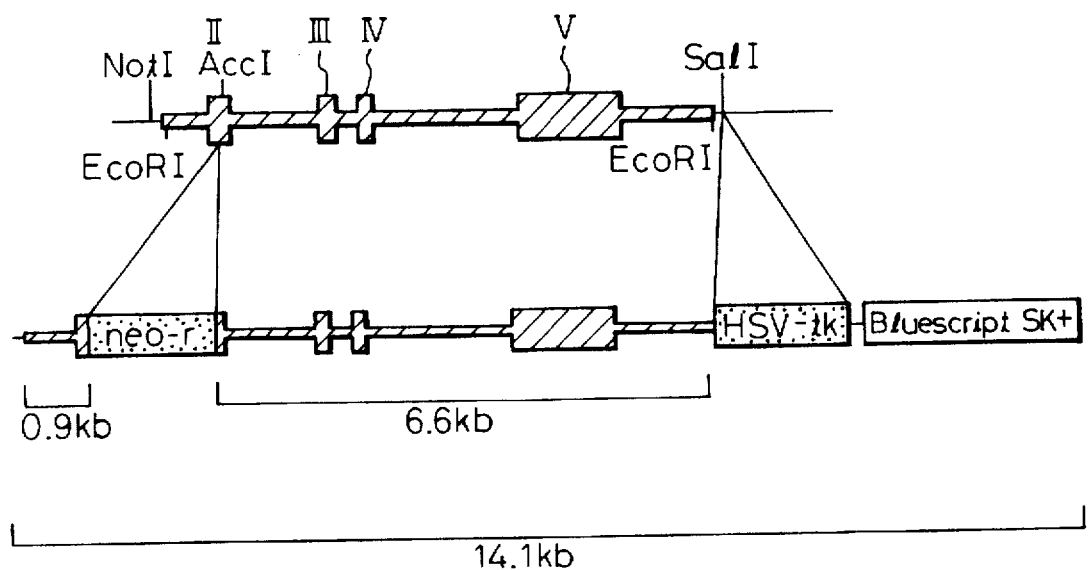
FIG. 2 shows the gene of FIG. 1 after insertion of a neomycin-resistance gene (neo$^r$) into exon No. 2 and a thymidine kinase gene (HSV-tk) downstream from exon No. 5.

Next, in order to destroy the structure of the ET-1 gene, a neomycin-resistance gene was inserted in exon No. 2 and a thymidine kinase gene was inserted downstream at the 3' end. The portions homologous with the genomic DNA were 0.9 kb upstream of the neomycin-resistance gene and 6.6 kb between the neomycin-resistance gene and the thymidine kinase gene. The construct for homologous recombination was inserted into pBluescriptSK+, and then was linearlized with restriction endonuclease NotI for transfection into the ES cells (FIG. 2).

(2) ET-1 gene deletion in ES cells by introduction of construct for homologous recombination A 150 μg portion of DNA construct for the homologous recombination was suspended in an electroporation buffer (20 mM HEPES, 137 mM NaCl, 5 mM KCl, 0.7 mM $Na_2HPO_4$, 6 mM dextrose, 0.1 mM mercaptoethanol) containing $1 \times 10^8$ cells of A3-1 strain, under conditions of a 2000 V/cm field strength and 3 μF capacitance, for introduction of the gene. Selection culture was then performed using 300 μg/ml of G418 (Genetisin, Sigma) at 24 hours after the introduction, and at 48 hours thereafter, 0.5 μg/ml of ganciclovir was also added and the selection culture was continued.

From 120 hours after the electroporation, the G418- and ganciclovir-resistant colonies were transferred to a 96-well microplate (Corning 25860MP) containing 60 μl of TE solution using a micropipette, and after a few minutes of treatment they were pipetted to leave single cells which were transferred to a 24-well microplate (Corning 25820GEL) for subsequent culture. The obtained colonies had a major axis which reached at least ½ of the inner diameter of the microchip, at which time the cell count was $1 \times 10^4$ to $10^5$. The number of surviving cells after the electroporation was $4.0 \times 10^7$. The number of G418- and ganciclovir-resistant cells was $2.8 \times 10^2$, which was $1/1.4 \times 10^5$ the number of surviving cells.

The cells on the 24-well microplate reached a confluent stage after 3 to 4 days in culture and were then subjected to TE treatment, after which they were successively cultured in a 35 mm (Corning 25000GEL) or 60 mm (Corning 25010GEL) tissue culturing petri dish for proliferation of the cells. All the culture of the ES cells was carried out on feeder cells. Identification of the homologous recombinants was carried out by PCR and Southern blotting in the following manner. A PCR primer was designed for amplification of a portion of about 1 kb between the 3' end of the homologous recombination construct and intron No. 1.

That is, a DNA synthesizer (BioRad) was used to synthesize oligonucleotides with the respective 24 mer base sequences 5'-GCAGATAAACTGCGCGCGATCTGT-3' (Sequence No.: 1) and 5'-AATCCATCTTGTTCAATGGCCGAT-3' (Sequence No.: 2), at the 5' upstream end 76 bp from the EcoRI recognition site of intron No. 1, and after treatment at 94° C. for 5 minutes, they were subjected to 40 cycles of amplification including DNA denaturation at 95° C. for 1 minute, primer annealing at 64° C. for 1 minute and primer extension at 72° C. for 1 minute, followed by a DNA extension reaction at 72° C. for 1 minute, and finally a 1 kb band was detected by agarose gel electrophoresis.

For the Southern blotting analysis, genomic DNA was extracted from the G418- and ganciclovir-resistant cells and digested with the restriction endonuclease SacI, and a 0.4 kb SacI-EcoRI fragment from intron No. 1 was used as the probe. The homologous recombinant and wild form were identified by detecting 3.1 kb and 4.4 kb bands, respectively. The number of homologous recombinant colonies was 35 of the 281 G418- and ganciclovir-resistant colonies ($1/1.1 \times 10^6$). There was complete agreement between the results of the PCR test and the Southern blotting analysis.

(3) ES cells and method of culturing

The ES cells used were A3-1 strain derived from 129/SvJ mouse blastocysts (Azuma & Toyoda, Jpn. J. Anim. Reprod. 37, 37–43, 1991). The ES cells were cultured in Dulbecco modified Eagle medium (DMEM, Cord, 430-2100, GIBCO)

supplemented with 20% fetal calf serum (FCS), 0.1 mM 2-mercaptoethanol, a nucleic acid mixture solution, a nonessential amino acid solution and $10^3$ unit/ml of LIF (AMRAD) (SCM culture medium (Robertson, Teratocarcinomas and Embryonic Stem Cells: A Practical Approach, 1987)).

Also, the mouse fetal fibroblasts used as feeder cells for the ES cells, were cultured in DMEM containing 10% FCS. The preparation and culture of the mouse fetal fibroblasts were carried out in the following manner. ICR mouse fetuses with a fetal age of 13–14 days were aseptically taken and washed with phosphate buffered physiological saline containing no calcium or magnesium (PBS$^-$), after which the hearts, livers and bowels were removed using forceps and morcellated using ophthalmic scissors. They were then treated at room temperature for 20 minutes with PBS$^-$ containing 0.25% trypsin and 0.04% EDTA (TE solution) to obtain a cell suspension.

The cell suspension was centrifuged at 1500 rpm for 5 minutes, its supernatant was removed off, and the cells were then suspended in 10% FCS-containing DMEM and allowed to stand for 2 minutes. The suspension from which the lower precipitated tissue fragments had been removed was then transferred to a 100×20 mm tissue culturing petri dish (Corning, 25020), and provided for culturing at conditions of 37° C., 5% $CO_2$ and 95% air. On the following day, washing was effected once with PBS$^-$, and culturing was continued. Subculturing was performed at 3–4 day intervals, and cells from the 1st–3rd generation of subculturing were subjected to mitomycin treatment for use as feeder.

The mouse fetal fibroblast cells which had grown to confluency were treated for 3–4 hours with 10 µg/ml of mitomycin C, washed 3 times with PBS$^-$, and then treated with TE solution at room temperature for 2 minutes to separate the cells. After centrifugation the cells were suspended at a density of $3×10^5$ cells/ml, of which 3 ml each was apportioned into 60×10 mm gelatin-coated dishes (Corning 25010 GEL). The feeder cells prepared in the manner described above were used within one week. The subculturing of the ES cells was carried out by TE treatment at room temperature for 5 minutes followed by dispersion to single cells by pipetting and then inoculation of $1×10^6$ cells onto a layer of feeder cells.

The culture medium was replaced at 24 hour intervals, and the subculturing interval was 56–64 hours. Also, for cryopreservation, $4–5×10^6$ cells were suspended in SCM and transferred to a serum tube (1.2 ml, Corning, 25703VIAL1) and 0.5 ml of freezing medium (20% DMSO-added DMEM) was added dropwise thereto, after which the mixture was allowed to stand overnight at −80° C. and then stored in liquid nitrogen.

(4) Preparation of chimeric mouse with endotheline gene-deficient ES cells a) Karyotype analysis of endotheline gene-deficient ES cells and assay of differentiation potency in suspension culture The endotheline gene-deficient ES cells in which homologous recombination had been confirmed was used to prepare a chromosome sample, and the proportion of cells with 2n=40 chromosomes, the normal mouse karyotype, was calculated. Colcemid (GIBCO) was added to cells at the 2nd day of subculturing to a final concentration of 0.1 µg/ml, and culturing was conducted for 1.5 hours.

After TE treatment, the cells were subjected to hypotonic treatment with 0.56% KCl solution for 30 minutes at room temperature and were fixed by 5 minutes' treatment at room temperature with methanol:acetic acid=3:1, and then centrifugation was repeated twice. The cells were then dropped with a small amount of the fixing fluid, and air dried overnight. After dyeing for 30 minutes with 10% Giemsa solution, the cells were microscopically examined. Of the 35 lines confirmed by PCR and Southern blotting to lack the endotheline gene, examination of the karyotypes of 17 lines showed a proportion of normal diploid of from 5% to 57%, of which 1 line was less than 10%, 7 lines were between 10% and 30%, 1 line was between 30% and 40%, and 8 lines were 40% or greater.

Differentiation was induced in vitro on the line with the highest proportion of normal diploids. 3 day-subcultured cells were subjected to TE treatment, and then allowed to stand for 30 minutes on a gelatin-coated dish to adhere the feeder cells on the bottom of the dish in order to collect the ES cells alone. A suspension of $6×10^6$ cells/ml was then prepared and cultured in suspension on a 100 mm bacterial dish using 10% FCS-added DMEM, and observed for embryoid body formation potency.

As for the judgment of embryoid body formation, the day on which at least 10 embryoid bodies were observed on the dish was defined as the day of embryoid body formation. The culture medium was replaced every 4 days. As a result, a simple embryoid body was found on the 4th day after culturing, and a cystic embryoid body was found on the 8th day after culturing.

b) Injection of endotheline gene-deficient ES cells into blastocysts

ES cells confirmed to be normal by karyotype analysis and assay of differentiation potency were injected into C57BL/6J mouse blastocysts which were then transferred into the uterine horn of pseudopregnant mice to obtain offspring. The embryos were obtained from donors on the 4th day of natural mating, by flushing of the uterus with Hepes-buffered Whitten's medium. The ES cells used for the injection had been subjected to TE treatment on the 2nd or 3rd subculturing, the feeder cells had been removed by the method described above, and had been stationed on ice until provided for the micromanipulation.

The injection pipette for the ES cells was a microglass tube (NARISHIGE) with an outer diameter of 1 mm which had been finely drawn using a microelectrode forming apparatus (NARISHIGE, PN-3), polished at the tip with a grinder (NARISHIGE) to an inner diameter of about 20 µm, and finally sharpened at the tip with a microforge (De Fonburun). The holding pipette was prepared by using a microforge to cut a glass tube drawn by the method described above at a section with an outer diameter of 50–100 µm, and then further finishing the aperture to 10–20 µm.

The injection pipette and holding pipette were bent at a section about 5 mm from the tip and connected to a micromanipulator (LEITZ). The chamber used for the micromanipulation was a perforated glass slide with a cover glass adhered thereto with wax, on which 2 drops of about 20 µl of 5% FCS-added Hepes-buffered Whitten's medium were placed and the top thereof covered with liquid paraffin (Art 7162, Merck). About 100 ES cells were placed on one of the drops, while 10–15 expanded blastocysts were placed on the other and 10–15 ES cells were injected per embryo.

All of the micromanipulation was performed with an inverted microscope. After 1–2 hours of culturing, the manipulated embryos were transferred into the uterine horn of ICR host females in the 2nd day of pseudopregnancy. The host females whose offspring were not delivered on the expected day of birth were subjected to caesarean section and raised by foster parents.

C31 ES cells were injected into 43 C57BL/6J mouse blastocysts taken by flushing of the uteri, and 32 of these survived for a success rate of 74%. Of these, 31 were transferred into the uterine horn of ICR host females in the 2nd day of pseudopregnancy, upon which 27 were found to be implanted, and 19 offspring were obtained. Of the 16 offspring which became weaned, 10 were judged by their coat color to be chimeric mice, and 9 of these were morintroduction of a neomycin-resistance gene and/or thymidine kinase gene into the endotheline-1 gene. This mouse is useful as an experimental animal for elucidation of the pathological physiology and causes of and development of therapies for cardiovascular diseases such as hypertension, arteriosclerosis and ischemic heart disease.

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( x i ) SEQUENCE DESCRIPTION: SEQ ID NO:1:

GCAGATAAAC TGCGCGCGAT CTGT      24

( 2 ) INFORMATION FOR SEQ ID NO:2:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( x i ) SEQUENCE DESCRIPTION: SEQ ID NO:2:

AATCCATCTT GTTCAATGGC CGAT      24 phologically male. The contribution ratio of ES cells in these chimeric mice ranged from 10 to 95%, with 3 cases having a contribution ratio of less than 60%, 2 cases between 60% and 90%, and 4 cases 90% or higher.

c) Crossing of chimeric mice

The chimeric mice obtained by embryo transfer were crossed with 129/SVJ or ICR mice and it was determined whether offspring derived from the endotheline gene-deficient ES cells were obtained. If the germ cells of the chimeric mice are derived from the homologous recombinant, then the coat color of the offspring is albino, while if they are derived from the blastocyst of C57BL/6J mice, it is the agouti color. To date, of 8 cases (Nos. 1, 2, 4, 5, 6, 7, 21, 23, 24), excepting 2 which died prior to reaching sexual maturity, the germ line transmission of the ES cells has been confirmed for 2 cases (No. 1, 5).

Upon breeding of No. 1 with an ICR female mouse, a total of 38 offspring were obtained of which 30 exhibited albino hair color. Also, of the 11 offspring obtained upon breeding of No. 5 with an ICR female, 3 were albino. Of these albino mice, 29 were analyzed by PCR and Southern blotting and 8 were confirmed to lack the endotheline-1 gene.

Mice according to the present invention may be easily produced by faithfully following the method described above.

INDUSTRIAL APPLICABILITY

As mentioned above, the present invention provides a mouse whose endotheline-1 gene has been destroyed by

We claim:

1. A process for producing a genetically engineered mouse having a disrupted endotheline-1 gene, said process comprising the steps of (a) preparing a DNA fragment comprising a disrupted endotheline-1 gene, wherein said endotheline-1 gene is disrupted by the insertion of a selectable marker sequence into exon No. 2 of the endotheline-1 gene;

(b) preparing embryonic stem cells from a mouse;

(c) rendering the endotheline-1 gene contained in the genome of the embryonic stem cells defective by transforming the embryonic stem cells with the DNA fragment of step (a), wherein the endotheline-1 gene in the embryonic stem cell genome is rendered defective by homologous recombination with the DNA fragment of step (a);

(d) culturing the cells of step (c);

(e) subjecting the cells of step (d) to a procedure selected from the group consisting of (I) karyotype analysis, (ii) assay of differentiation potency and (iii) karyotype analysis and assay of differentiation potency;

(f) selecting the cells of step (e) that have characteristics selected from the group consisting of (I) normal karyotype, (ii) normal differentiation potency and (iii) normal karyotype and normal differentiation potency;

(g) generating chimeric mice from the cells of step (f) by injecting said cells into mouse blastocysts and transferring said blastocysts into pseudopregnant mice; and (h) breeding said chimeric mice to produce a genetically engineered mouse having a disrupted endotheline-1 gene, wherein said disrupted endotheline-1 gene results in said mouse exhibiting altered hemodynamics as compared to a wild-type mouse.

2. A process according to claim 1, wherein said selectable marker sequence is a neomycin-resistance gene.

3. A process according to claim 2, wherein said neomycin-resistance gene is inserted into exon No. 2 of the endotheline-1 gene.

4. A genetically engineered mouse having a disrupted endotheline-1 gene, wherein said mouse is produced by the process according to claim 1, and wherein said disrupted endotheline-1 gene results in said mouse exhibiting altered hemodynamics as compared to a wild-type mouse.

5. A genetically engineered mouse having a disrupted endotheline-1 gene, wherein said endotheline-1 gene is disrupted by the insertion of a selectable marker sequence into exon No. 2 of the endogenous endotheline-1 gene of said mouse, wherein said selectable marker sequence is introduced into said mouse or an ancestor of said mouse at an embryonic stage, and wherein said disrupted endotheline-1 gene results in said mouse exhibiting altered hemodynamics as compared to a wild-type mouse.

* * * * *